United States Patent
Slettenmark

(10) Patent No.: US 6,230,042 B1
(45) Date of Patent: May 8, 2001

(54) METHOD AND ARRANGEMENT FOR DETERMINING THE LOCATION OF A CATHETER WITHIN AN ANIMAL BODY

(75) Inventor: Bruno Slettenmark, Järfälla (SE)

(73) Assignee: Siemens Elema AB, Sundyberg (SE)

( * ) Notice: Subject to any disclaimer, the term of this patent is extended or adjusted under 35 U.S.C. 154(b) by 0 days.

(21) Appl. No.: 09/257,255

(22) Filed: Feb. 25, 1999

(30) Foreign Application Priority Data

Mar. 25, 1998 (SE) .................................................. 9801006

(51) Int. Cl.$^7$ .......................................................... A61B 5/00
(52) U.S. Cl. ................................................................ 600/424
(58) Field of Search .................................................... 600/524

(56) References Cited

U.S. PATENT DOCUMENTS 5,042,486   8/1991   Pfeiler et al. .
5,676,673   10/1997  Ferre et al. .
5,724,978   3/1998   Tenhoff .

FOREIGN PATENT DOCUMENTS

WO 96/31753   10/1996   (WO) .
WO 98/00060   8/1998    (WO) .

*Primary Examiner*—William E. Kamm
(74) *Attorney, Agent, or Firm*—Hill & Simpson

(57) ABSTRACT

A catheter arrangement has an active catheter, positionable in a vessel or organ of an animal, having at least one transducer disposed proximal the catheter tip; and a fixed catheter, also positionable within the animal in the vicinity of the active catheter, carrying a number of reference transducers. A signal processing unit is arranged to selectively operate the transducers to send and receive signals between the active and fixed catheters. The signal processing unit operates to calculate from the received signals at least two independent locations of the active catheter relative to the fixed catheter and to combine the independently calculated locations to provide a weighted average determination of the location in which the relative contributions of the calculated locations to the determined location decrease as their associated error values increase.

8 Claims, 5 Drawing Sheets

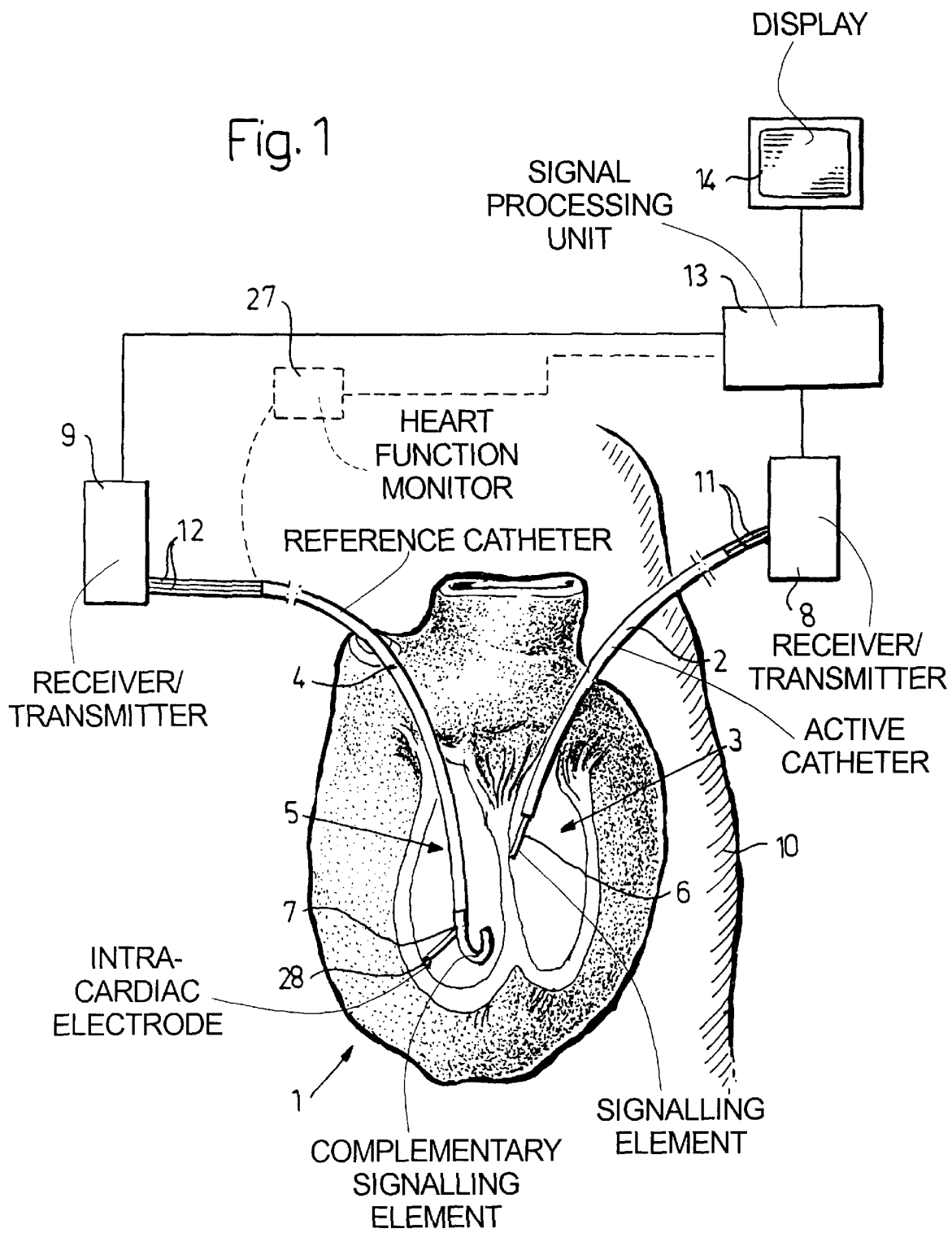

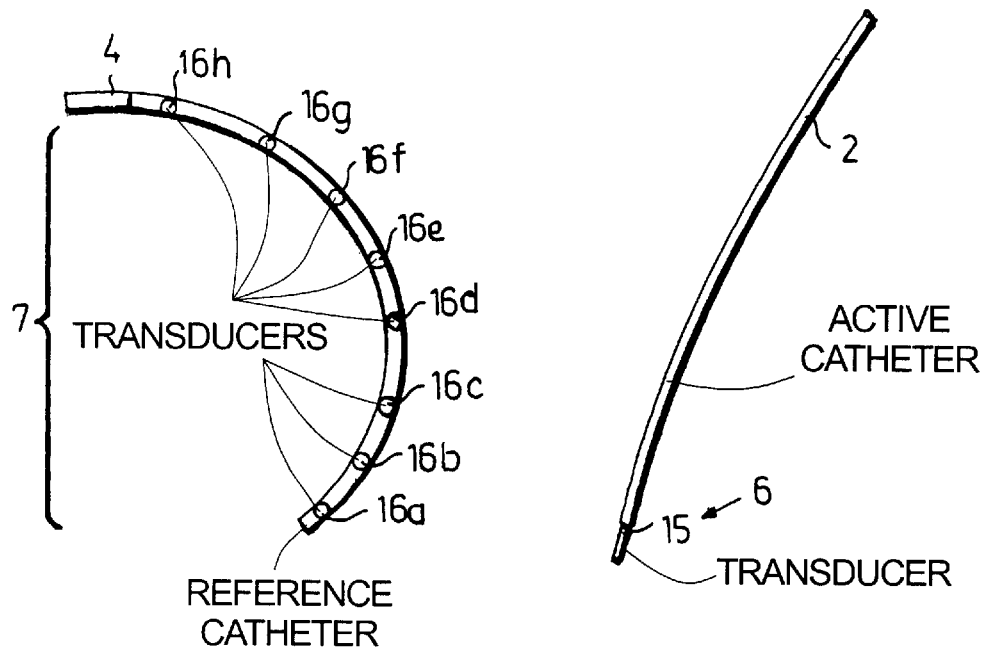
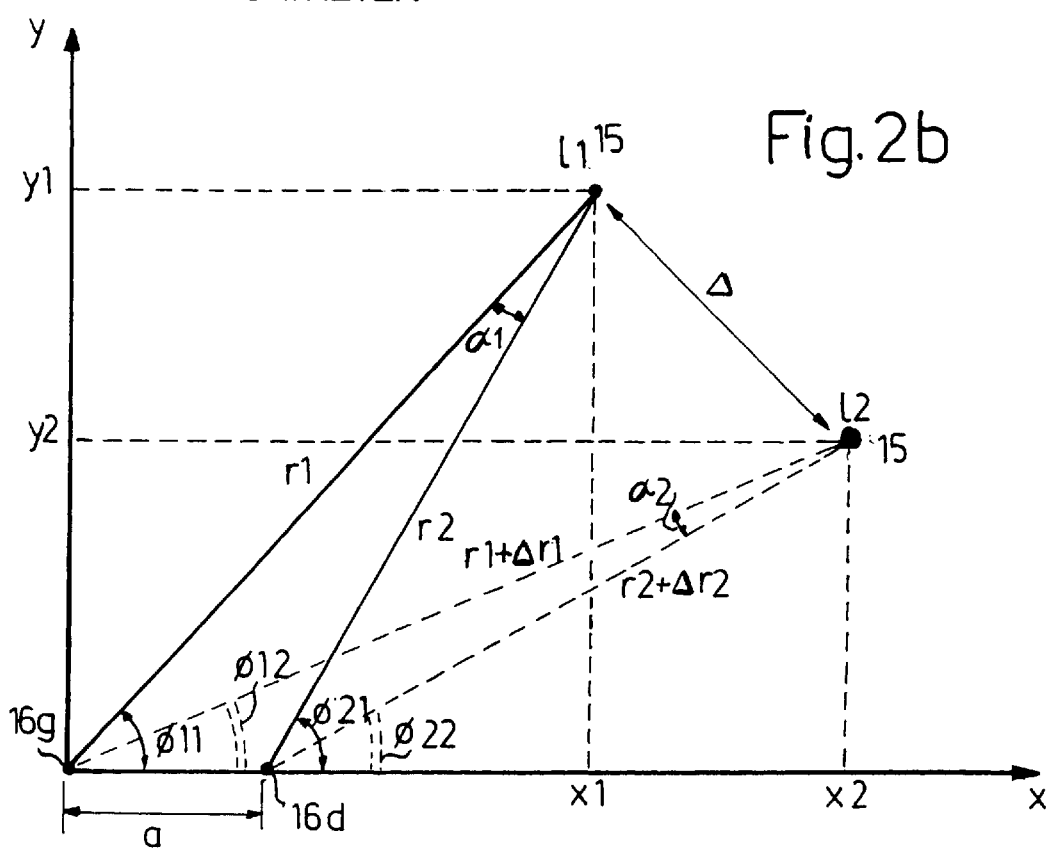

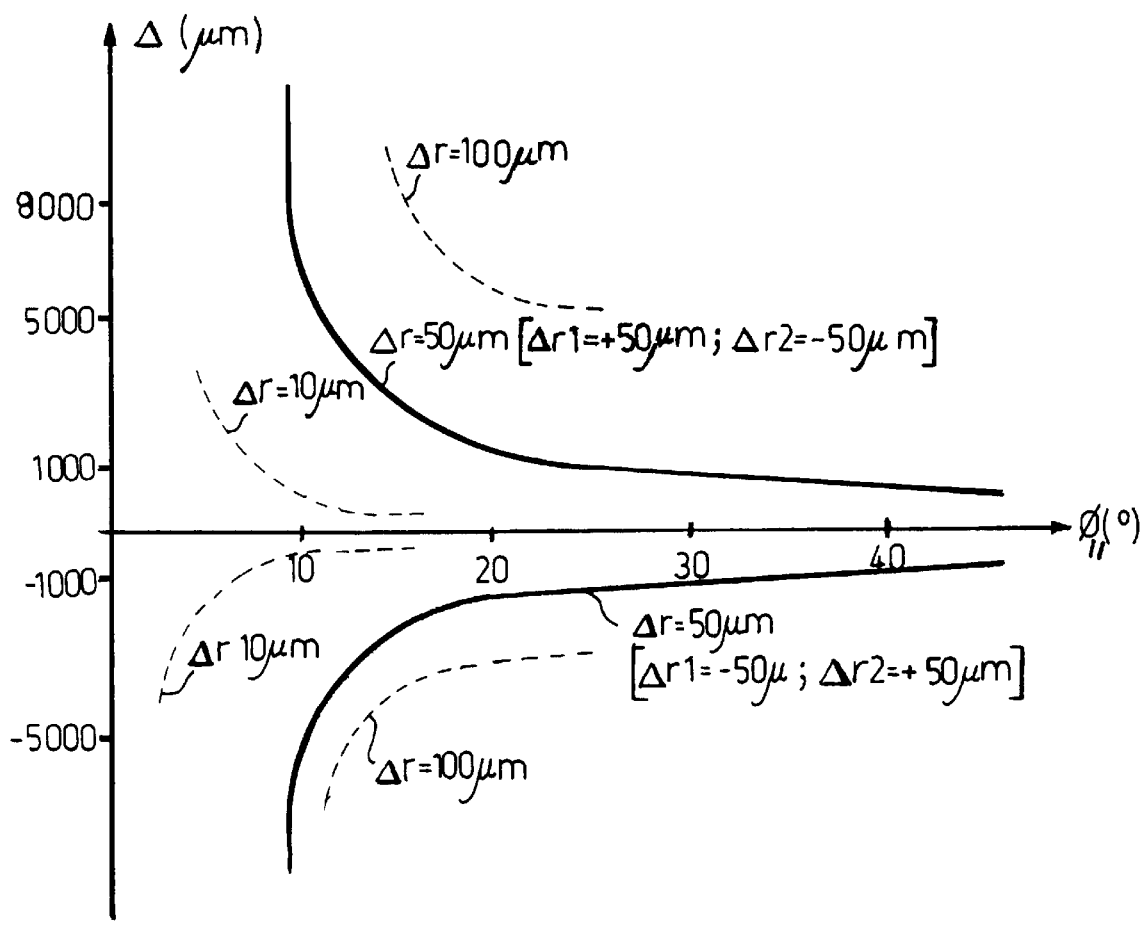

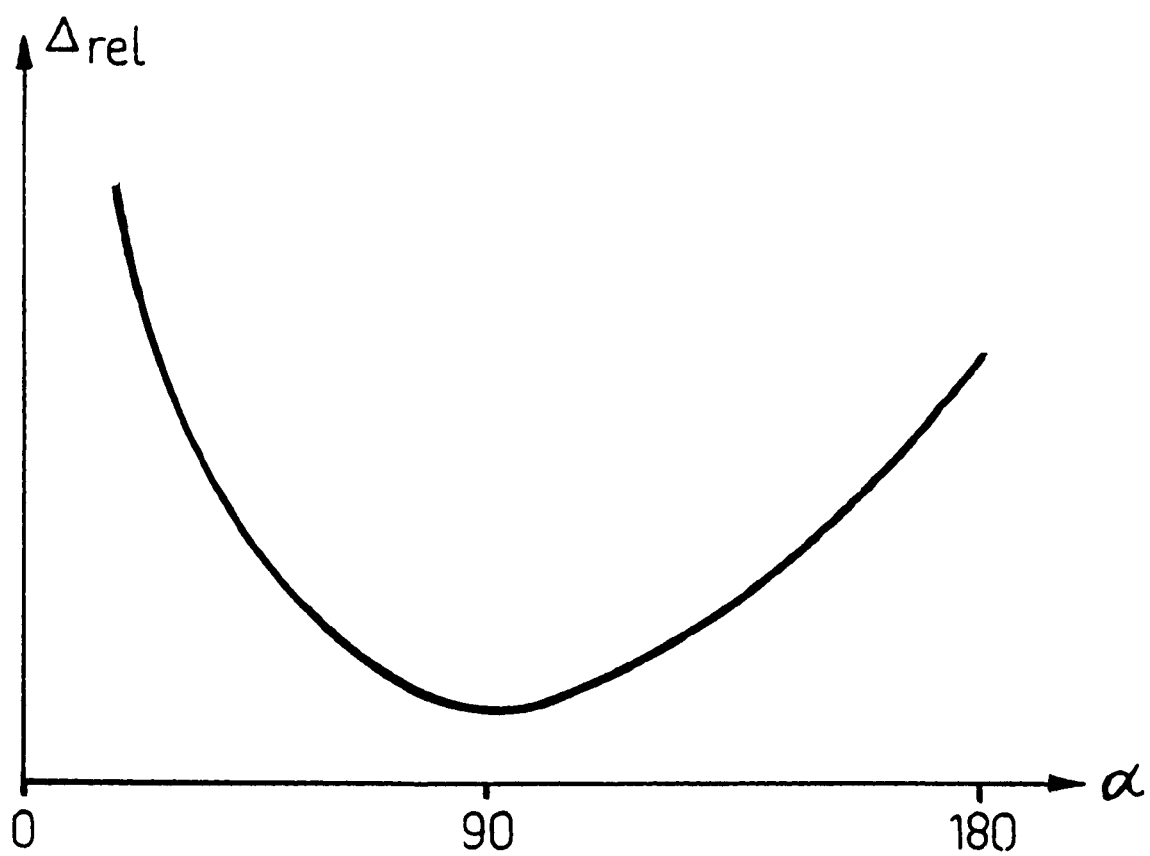

METHOD AND ARRANGEMENT FOR DETERMINING THE LOCATION OF A CATHETER WITHIN AN ANIMAL BODY

BACKGROUND OF THE INVENTION

1. Field of the Invention

The present invention relates to a method and arrangement for determining the location of an active (i.e. a measurement and/or treatment) catheter within an animal (including human) body and in particular to such a method and arrangement of the type employing triangulation techniques in order to make the determination.

2. Description of the Prior Art

Systems for locating a catheter within an animal body using triangulation are well known and such a system is described, for example, in U.S. Pat. No. 5,042,486. In this known system, an electromagnetic or acoustic signal is transmitted between an antenna at the tip of an active catheter and three reference antennas placed on the outside of the animal. The distances between each reference antenna and the catheter antenna are then combined, using triangulation methods, to provide a determination of the active catheter in three-dimensions.

For many medical applications it is desirable to be able to locate an active catheter in a patient, e.g. in angiographic examinations and in cardiac diagnostics and therapy, with as high a degree of accuracy as possible.

One system that is used to locate such an active catheter with an improved accuracy is disclosed in PCT Publication WO 98/00060, and has a fixed reference catheter and an active catheter, between which acoustic or electromagnetic signals are transmitted. The transmitted signals are used to measure the distance between transducers mounted on the reference catheter and at least one transducer mounted on the active catheter. The location of the catheter is determined by triangulation. In the system described in WO 98/00060 both the reference and the active catheter are positioned inside the patient, with the consequence that the position measurements may be made more accurately since they are not affected by the movement or breathing of the patient. WO 98/00060 also describes a system in which the number of transducers that are mounted on the reference catheter exceeds the minimum number of transducers required mathematically to make the location determination. In this way a number of independent determinations of the catheter location may be made by using a different combination of reference transducers for each determination. An averaged location may then be calculated having an increased accuracy over a single determination.

Similarly, WO 96/31753 describes a digital ultrasound catheter tracking system that can employ up to 32 transducers to create a redundancy in distance measurements so that the three-dimensional location of the catheter can be determined even if some distance measurements are ignored, for example because of poor signal propagation through the measurement volume.

Nevertheless, even when using a system in which a greater number of distances are measured than are mathematically required to locate the catheter, the determined location may still have a relatively large error associated with it.

SUMMARY OF THE INVENTION

An object of the present invention is to provide a method and arrangement for determining the location of an active catheter wherein the above disadvantage associated with known systems is reduced.

The above object is achieved in accordance with the principles of the present invention in a method and arrangement for determining the location of a catheter within a living body, wherein a distance between the catheter and a number of reference cites within the living body is measured, wherein at least two independent calculations of the location of the catheter are made, using triangulation, from the measured distances, and wherein the location of the catheter is determined using these independent calculations, by generating a weighting for each independently calculated location dependent on an error value associated with the calculation for that location, and by combining the weighted independent calculations thereby reducing the relative contributions of the independently calculated locations as their respectively associated error values increase.

Thus in the present invention a number of individually calculated locations are combined to provide an average location value in which the contribution of each calculated location to the average value reduces, as its error increases. The potential for determining a location having a large standard deviation is thereby reduced.

The method includes, for a number of calculated locations greater than 1, the step of reducing to zero the contribution of calculated locations having error values which exceed a predetermined maximum value. In this way the most inaccurate calculated locations may be eliminated from further consideration.

Preferably the method includes calculating the measurement error associated with each calculated location and generating an average location in which the contribution of each calculated location reduces as its calculated error increases.

DESCRIPTION OF THE DRAWINGS

FIG. 1 is a schematic representation of a catheter arrangement according to the present invention.

FIG. 2a schematically illustrates a distal end of a reference catheter for use in the method and arrangement of the invention.

FIG. 2b schematically illustrates the distal end of an active catheter used in the method and arrangement of the invention.

FIG. 2c illustrates an example of determining the location of a catheter using triangulation from the measurements made using the catheters shown in FIGS. 1, 2a and 2b.

FIG. 3 indicates for the two dimensional case, the variation $\Delta$ of location determination with angle $\phi 11$ for a given maximum distance determination error $\Delta r$, of $\pm 50$ $\mu$m together with an indication of how this variation changes with $\Delta r$.

FIG. 4 shows generally how $\Delta_{REL}$ varies with angle $\alpha$.

DESCRIPTION OF THE PREFERRED EMBODIMENTS

Figure 5A:
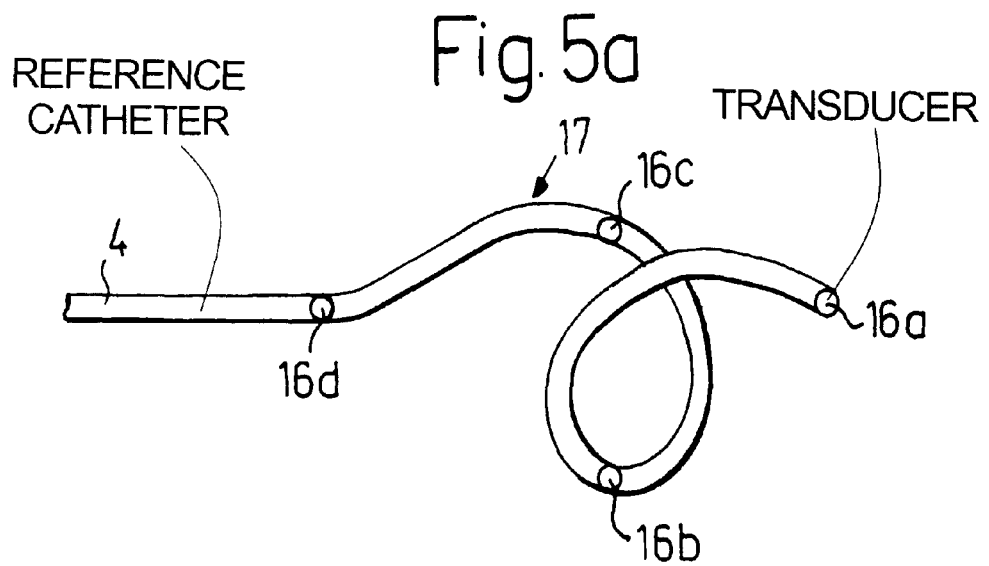
FIGS. 5a, 5b and 5c respectively illustrate alternative shapes for the reference catheter usable in the arrangement of FIG. 1.

Referring to FIG. 1, a part of a patient's heart 1 is shown with an active catheter 2 introduced into one of the heart chambers 3 and a reference catheter 4 introduced into the other heart chamber 5.

The active catheter 2 is provided with signaling element 6 near its distal tip, which lies proximal the heart chamber 3. A complementary signaling element 7 is disposed on the portion of the reference catheter 4 that lies within the other heart chamber 5. The signaling element 6 can be a signal transmitter, in which case the complementary signaling element 7 will be a signal receiver. Alternatively, the signaling element 6 can be a receiver and the complementary signaling element 7 can be a transmitter.

As shown, programmable receiver/transmitters 8,9 are placed external the patient's body 10 and are operably connected to their respective signal transmitting and/or receiving elements 6,7 via electrical conductors 11,12. A signal processing unit 13, which may be a suitably programmed microprocessor, is connected to each programmable receiver/transmitter 8,9 to selectively control the operation of the receiving and/or transmitting elements 6,7 so that a signal emitted from one catheter can be received and detected by the other. Additionally the signal processing unit 13 operates to determine the location of the active catheter 2 relative to the reference catheter 4 from the signals transmitted between these catheters 2,4, as will be described in more detail. A display 14 is connected to the signal processing unit 13 to present a visual representation of the determined location of the active catheter 2.

It will be appreciated by those skilled in the art that an arrangement having such selectively programmable signal transmitting and receiving elements provides a greater flexibility of use than one in which the operation of each element is fixed. However, for increased clarity all further descriptions will assume that the signaling element 6 of the active catheter 2 operates as a signal transmitter and that the signaling element 7 of the reference catheter 4 acts as a complementary signal receiver.

Preferably a heart function monitor 27 is also provided in operable connection with the signal processing unit 13, as shown by the broken lines in FIG. 1. This heart function monitor 27 may include external ECG electrodes or, as shown, an internal, intra-cardiac electrode 28 which for convenience may be a part of the reference catheter 4. The signal processing unit 13 may then be constructed to synchronize the operation of the receiving element 7 and transmitting element 6 means with a fixed position in the cardiac cycle so that the signal is always transmitted between the catheters 2,4 with the heart 1 in the same geometrical and geographical disposition. This is a conventional operating arrangement, used in known catheter location systems, and need not be described further here.

FIGS. 2a, 2b and 2c illustrate the principle of operation of the embodiment of FIG. 1. In FIG. 2b the active catheter 2 is provided with transmitting element 6 in the form of an ultrasound transducer 15, which may be a transceiver, (a second ultrasound transducer may be provided on the active catheter 2 if the orientation as well as the location of the catheter is needed). As shown in FIG. 2a, the reference catheter 4 is provided with receiving element 7 formed by a number of transducers 16a . . . 16h. The number of reference transducers is chosen so that at least two independent calculations of the location of the active catheter 2 may be made. When in position, the portion of the reference catheter 4 carrying the transducers 16a . . . 16h is curved in a controlled and stable manner so that the transducers 16a . . . 16h do not all lie in a straight line, and preferably lie in different planes, in order to improve the position determination accuracy.

Figure 5B:
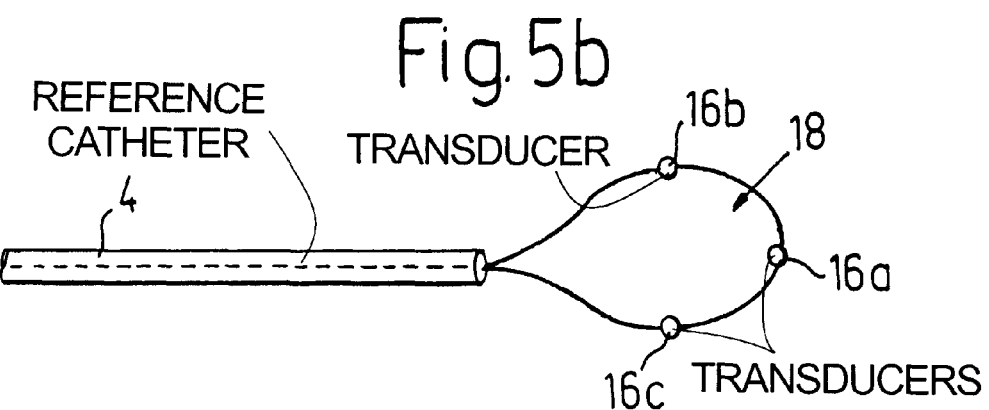
Figure 5C:
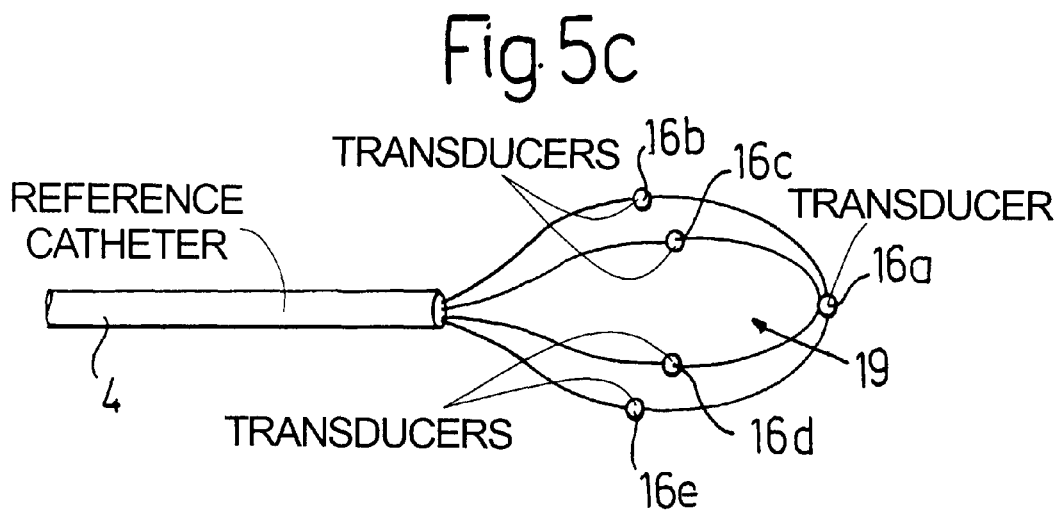

As disclosed in WO 98/00060, the requirements of the reference catheter can be realized using catheters configures other than that shown in FIG. 2a, for example a catheter having a double-curved, helical tip portion, as shown in FIG. 5a, may be used. Here a helical three-dimensional ultrasound transducer carrier 17 is formed on the distal end of the reference catheter 4 and carries at least three reference transducers, shown here as 16a . . . 16d. This distal end may be formed of a memory alloy adapted to form the desired shape of the carrier 17 after introduction into the vessel or organ in question. Alternatively, known loop catheter 18 or a basket catheter 19 may be used as illustrated in FIGS. 5b and 5c respectively.

Moreover, if the reference transducers 16a . . . 16h can be selectively operated by the signal processing unit 13 to act alternately as a transmitter and a receiver, signals may be emitted from one of the reference transducers 16a for receipt by all other reference transducers 16b . . . 16h and the relative location of 16a with respect to the other reference transducers 16b . . . 16h can be determined by the signal processing unit using triangulation as discussed below in relation to locating the active catheter 2. The relative locations of all reference transducers 16a . . . 16h may be similarly determined. This avoids the need to know the exact shape of the tip portion of the fixed catheter 4 on which the reference transducers 16a . . . 16h are disposed.

In use, short duration ultrasound pulses, preferably in the frequency range of 10–30 MHZ, are transmitted from the transducer 15 and the transit times (time of flight) of these pulses to the transducers 16a . . . 16h are measured in the signal processing unit 13 of FIG. 1, these transit times are a direct measure of the distances between the transmitting and receiving transducers and the signal processing unit 13 and are used by the processing unit 13 to determine the location of the transducer 15 based on the following:

Considering FIG. 2c and a triangle formed between any two transducers 16a . . . 16h (shown as 16g and 16d), separated by a known distance a on the reference catheter 4, and the transducer 15 on the active catheter 2. For simplicity only the two dimensional case is considered where all transducers lie in one plane (shown as the x-y plane) and typical values of a=5 mm; r=40 mm are assumed. The example also uses $\phi 11=11°$ and an error in distance determinations of $\Delta r1=+\Delta r=50 \mu m$ and $\Delta r2=-\Delta r=-50 \mu m$; where $\Delta r1$ and $\Delta r2$ represent the actual errors involved in the distance measurements of r1 and r2 respectively. $\Delta r$ is the maximum possible error in the distance measurements of r1 and r2 (50 $\mu m$ in this example) then the error, $\Delta$, in determining the position, 1, may be determined from simple trigonometric relations of the type given below for the present case whereby:

$$\phi 11 = \cos^{-1}[(a^2+r1^2-r2^2)/(2 \cdot a \cdot r1)] \quad (1)$$

$$\phi 12 = \cos^{-1}[(a^2+(r1+\Delta r1)^2-(r2+\Delta r2)^2)/(2 \cdot a \cdot (r1+\Delta r1))] \quad (2)$$

$$\phi 21 = \cos^{-1}[(r1^2-r2^2-a^2)/(2 \cdot a \cdot r2)] \quad (3)$$

$$\phi 22 = \cos^{-1}[((r1+\Delta r1)^2-(r2+\Delta r2)^2-a^2)/(2 \cdot a \cdot (r2+\Delta r2))] \quad (4)$$

$$r2 = (r1 \cdot \sin \phi 11)/\sin \phi 21 \quad (5)$$

$$\alpha = \cos^{-1}[(r1^2+r2^2-a^2)/(2 \cdot r1 \cdot r2)] \quad (6)$$

$$x1 = r1 \cdot \cos \phi 11 \quad (7)$$

$$x2 = (r1+\Delta r1) \cdot \cos \phi 12 \quad (8)$$

$$y1 = r1 \cdot \sin \phi 11 \quad (9)$$

$$y2 = (r1+\Delta r1) \cdot \sin \phi 12 \quad (10)$$

$$\Delta = [(x1-x2)^2+(y1-y2)^2]^{1/2} \quad (11)$$

to give Δ=6.033 mm and indicates that a small error in the measurement of the distance can lead to a substantial absolute error in the determination of the position. This description can easily be extended to the three dimensional case but is not done so here as it considered that the description of the operating principle would be detracted from by the necessarily more complex trigonometric considerations.

FIG. 3 indicates by the solid lines how this error Δ varies as the angle φ11 varies for the case discussed above. Also shown by the broken lines is how these curves vary dependent on the error, Δr, in the distance measurement r1. It can be seen that the error Δ generally increases as Δr increases and that the variations of Δ with angle φ11 change less steeply as Δr increases. Additionally, the solid line (Δr=50 μm) shows that the error Δ is asymmetric about the φ11 axis for the two curves, Δr1=+50 μm; Δr2=−50 μm (case illustrated in FIG. 2c) and Δr1=−50 μm; Δr2=+50 μm.

Now, for every triangle from which a position determination of the transducer 15 on the active catheter 2 is made the error Δ can be determined using suitable combinations of the equations 1 to 11 above using all four combinations of Δr1 and Δr2=±Δr (i.e. Δr1=+Δr, Δr2=−Δr; Δr1=−Δr, Δr2=+Δr etc.), one of which combinations will provide a maximum possible value for the location error, $\Delta_{MAX}$. This maximum location error may then be used in the signal processing unit 13 during a calculation of a "weighted average" location.

Thus the signal processing unit 13 of FIG. 1 may be programmed, using common programing techniques to make a number of independent location calculations, by triangulation as above, using triangles formed from all combinations of pairs of reference transducers 16a . . . h with the transducer 15 on the active catheter 2 and for each calculated location determining the maximum error value $\Delta_{MAX}$. The signal processing unit 13 may then be programmed to weight each calculated location according to $\Delta_{MAX}$ and to determine a "weighted" average location in which a calculated location having a small maximum error value contributes relatively more to the weighted average than a calculated location having a large maximum error value. In this way the weighted average location provides a more accurate value than would be the case had the calculated locations been simply averaged. Alternatively or additionally the signal processing unit 13 may be configured to reduce to zero the contribution of calculated locations having error values, Δ or $\Delta_{MAX}$, which exceed a predetermined value. In this way the most inaccurate calculated locations may be eliminated from further consideration.

As an alternative to calculating the $\Delta_{MAX}$ values the signal processing unit 13 may be provided with memory means in which a so-called "look-up table" is stored comprising a large number of $\Delta_{MAX}$ or weighting values corresponding to the majority of triangles typically used. The signal processor 13 may then be programmed to find the "typical" triangle that most closely matches the actual triangle in shape and size and to use the corresponding stored $\Delta_{MAX}$ or weighting value in the subsequent calculation of the weighted average location.

In the above example Δr, the maximum error in measuring the distances r1 and r2, has been taken to be a fixed value. In reality Δr may vary with either or both of the distance and the direction of travel of the signal. This is mainly because of variations in sound velocity that may occur because of differences in the material through which the signal travels. In a refinement of the above described method and arrangement values of Δr for different distances and for different materials of interest may also be stored in, or calculated by, the signal processing unit 13 using a suitable model for velocity variations, for example as may be readily constructed from empirical measurements of velocities through different media likely to be encountered in the body, and employed as described above.

In a further alternative to the arrangement described above the signal processing unit 13 may be programmed to determine a weighting dependent on the relative error $\Delta_{REL}$ in the calculation of the location, 1, which itself is dependent on the angle α, as shown generally in FIG. 4. It can seen that relative error $\Delta_{REL}$ increase as a approaches a and 180° and is a minimum when a is 90° and that $\Delta_{REL}$ increases more rapidly as it approaches 0° than as it approaches 180°. This angle α can be calculated relatively quickly by the suitable programming of the signal processing unit 13 and using equation (6) above and the actually measured distances r1 and r2. It will also be clear that when the average measured distance (i.e. (r1+r2)/2) is small then the absolute error Δ will be small and conversely when the average measured distance is large the absolute error Δ will be large. This will be accentuated by the fact that, as discussed above, Δr increases with distance. Therefore the signal processing unit 13 may be programmed to use weightings based upon the values of α and/or the average measured distance, either from calculations or from look up tables. From the above the optimum weighting selection will be from the combined knowledge of a and the average measured distance.

The above embodiments have been described using catheters located in different chambers of the heart but it will be clear to those skilled in the art that the catheters may be disposed in the same heart chamber or used within other bodily structures or organs without departing from the invention and that the reference transducers may be located directly on the heart or other vessel or organ without being first mounted on a catheter.

Moreover, it will also be apparent that the weightings may be calculated and applied to generate weighted average spatial co-ordinates (X and Y in the two dimensional case described above) in order to generate the weighted average location.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining a location of a catheter in an animal body, comprising the steps of:

providing a plurality of reference cites in a body;

measuring a distance between a catheter and said plurality of reference cites, thereby obtaining a plurality of measured distances;

making at least two independent calculations of a location of said catheter from said measured distances using triangulation;

associating respective error values with said at least two independent calculations;

assigning respective weighting values to said at least two independent calculations, said respective weighting values varying inversely relative to the respective error values, and thereby obtaining a plurality of weighted calculations; and determining the location of said catheter by combining said plurality of weighted calculations.

2. A method as claimed in claim 1 wherein the step of assigning respective weighting values to said at least two independent calculations comprises measuring an absolute magnitude of a positional error in an independent calculation and assigning said weighting value dependent on said absolute magnitude of said positional error.

3. A method as claimed in claim 1 wherein the step of assigning respective weighting values to said at least two independent calculations comprises determining an angle of convergence on said catheter of straight lines proceeding between said catheter and respective reference cites used in said triangulation, and assigning the weighting value to an independent calculation dependent on said angle.

4. A method as claimed in claim 3 comprising determining an average measured distance of the respective distances between said catheter and said reference cites used in said triangulation, and assigning said weighting value dependent on said average.

5. A method as claimed in claim 1 wherein the step of combining said weighted calculations comprises for a plurality of weighted calculations greater than one, discarding said weighted calculation if the error value associated therewith exceeds a predetermined value.

6. A method for determining a position of a catheter tip within an animal body, comprising the steps of:

introducing into an animal body a catheter having a catheter tip and carrying at least one transducer disposed proximate said catheter tip;

disposing a plurality of spaced-apart reference transducers within said animal body;

transmitting respective signals between said at least one transducer and each of said reference transducers and measuring respective distances traveled by said respective signals between said at least one transducer and each of said reference transducers, thereby obtaining a plurality of measured distances;

making at least two independent calculations of a location of said catheter from said measured distances using triangulation;

assigning an error value to each of said at least two independent calculations;

assigning a weighting value to each of said at least two independent calculations, said weighting value varying inversely relative to said error value for the independent calculation associated therewith, thereby obtaining a plurality of weighted calculations; and determining a location of said catheter by combining said plurality of weighted calculations.

7. A catheter arrangement comprising:

an active catheter adapted for implantation in an animal body, said active catheter having a catheter tip and carrying at least one transducer disposed proximate said catheter tip;

a fixed catheter adapted for implantation in an animal body carrying a plurality of reference transducers;

a signal processing unit including means for selectively operating said at least one transducer and said plurality of reference transducers to transmit and receive signals between said at least one transducer and said plurality of reference transducers, thereby obtaining a plurality of received signals;

said signal processing unit including means for calculating, from said received signals, at least two independently calculated locations of said active catheter relative to said fixed catheter; and said signal processing unit including means for assigning respective error values to said at least two independently calculated locations and for combining said at least two independently calculated locations to produce a weighted average determination of the location of said active catheter to which each of said at least two independently calculated locations contribute inversely relative to their respective error values.

8. An arrangement as claimed in claim 7 wherein said signal processing unit comprises means for assigning a weighted value to each of said independently calculated locations dependent on the respective error value associated therewith, to obtain a plurality of weighted calculations, and means for combining said weighted calculations dependent on their respective weighted values to produce said weighted average.

* * * * *